(12) United States Patent
Sherry et al.

(10) Patent No.: US 8,907,284 B2
(45) Date of Patent: Dec. 9, 2014

(54) TERAHERTZ IMAGER WITH GLOBAL RESET

(71) Applicant: STMicroelectronics S.A., Montrouge (FR)

(72) Inventors: Hani Sherry, Grenoble (FR); Andreia Cathelin, Laval (FR); Ullrich Pfeiffer, Wuppertal (DE); Janusz Grzyb, Hilden (DE); Richard Al Hadi, Wuppertal (DE)

(73) Assignee: STMicroelectronics S.A., Montrouge (FR)

( * ) Notice: Subject to any disclaimer, the term of this patent is extended or adjusted under 35 U.S.C. 154(b) by 135 days.

(21) Appl. No.: 13/692,691

(22) Filed: Dec. 3, 2012

(65) Prior Publication Data

US 2014/0151561 A1 Jun. 5, 2014

(51) Int. Cl.
*G01J 5/00* (2006.01)
*G01J 5/02* (2006.01)
*G01J 5/34* (2006.01)
*H03K 3/03* (2006.01)
*G05F 3/26* (2006.01)

(52) U.S. Cl.
CPC ............... *G01J 5/34* (2013.01); *H03K 3/0315* (2013.01); *G05F 3/26* (2013.01)
USPC ........ 250/338.1; 250/340; 250/349; 348/607; 348/E7.052

(58) Field of Classification Search
CPC ........... H03K 3/0315; G01J 5/34; G05F 3/26; H03F 1/26; H03F 3/45632
USPC .......... 250/340, 338.1, 349; 348/607, E7.052
See application file for complete search history.

(56) References Cited

U.S. PATENT DOCUMENTS

| 2005/0125181 A1* | 6/2005 | Norman et al. ............... 702/107 |
| 2008/0251721 A1* | 10/2008 | Ueno ............................ 250/332 |
| 2014/0151768 A1 | 6/2014 | Pfeiffer et al. |

* cited by examiner

*Primary Examiner* — David Porta
*Assistant Examiner* — Jeremy S Valentiner
(74) *Attorney, Agent, or Firm* — Allen, Dyer, Doppelt, Milbrath & Gilchrist, P.A.

(57) ABSTRACT

A pixel circuit may include a detection circuit having first and second transistors coupled in series between differential output nodes of an antenna. The antenna may be configured to be sensitive to terahertz radiation. The pixel circuit may also include a capacitor coupled to an intermediate node between the first and second transistors, and control circuitry coupled to control nodes of the first and second transistors. The control circuitry may be configured for selectively applying to the control nodes a gate biasing voltage for biasing the control nodes of the first and second transistors during a detection phase of the pixel circuit, and/or a reset voltage for resetting a voltage stored by the capacitor.

15 Claims, 3 Drawing Sheets

TERAHERTZ IMAGER WITH GLOBAL RESET

BACKGROUND

1. Technical Field

The present disclosure relates to the field of terahertz imagers, and in particular to a terahertz imager and method including a reset function.

2. Discussion of the Related Art

A terahertz (THz) imager is an image sensor adapted to capture an image of a scene based on waves in the terahertz frequency range. In general, terahertz waves are considered to comprise waves having a frequency of between 300 GHz and 3 THz. These frequencies, for example, correspond to wavelengths of one millimeter or less. For example, a 1 THz wave has a wavelength of approximately 300 μm.

Terahertz imagers are used widely for applications in which it is desirable to "see through" certain materials. In particular, terahertz waves have good penetrability in many dielectric materials and non-polar liquids. They are however almost entirely reflected by metals and absorbed by water molecules. This makes terahertz imagers particularly suited for applications such as in the security scanners used at airports and in devices used to analyze works of art. The wavelength is in general short enough to achieve good spectral resolution for imaging, but long enough such that the waves are scattered relatively little by air particles such as dust or smoke.

Due in part to a high frequency of the terahertz signal, and also to the relatively small signal strength that should be captured by the terahertz imager, there is generally a need in the art to improve the image quality of terahertz imagers.

SUMMARY

It is an aim of embodiments of the present disclosure to at least partially address one or more needs in the art.

According to one aspect, there is provided a pixel circuit comprising: a detection circuit having first and second transistors coupled in series between differential output nodes of an antenna, wherein said antenna is configured to be sensitive to terahertz radiation; a capacitor coupled to an intermediate node between said first and second transistors; and control circuitry coupled to control nodes of said first and second transistors, the control circuitry being configured for selectively applying to said control nodes one of: a gate biasing voltage for biasing the control nodes of the first and second transistors during a detection phase of the pixel circuit; and a reset voltage for resetting a voltage stored by said capacitor.

According to an embodiment, the control circuitry comprises: a third transistor coupled between said gate biasing voltage and the control nodes of said first and second transistors and having a control node coupled to a selection signal; and a fourth transistor coupled between said reset voltage and the control nodes of said first and second transistors and having a control node coupled to said selection signal.

According to another embodiment, one of the third and fourth transistors is a p-channel MOS transistor and the other of the first and second transistors is an n-channel MOS transistor.

According to another embodiment, the biasing voltage is in the range −0.4 V to 0.8 V, and the reset voltage is, for example, in the range 1 V to 2 V.

According to another embodiment, the intermediate node is coupled to a first column line.

According to another embodiment, the pixel circuit further comprises: a blind detection circuit having fifth and sixth transistors coupled in series between first and second nodes, said first and second nodes each being coupled to a biasing voltage of said antenna; and a capacitor coupled to an intermediate node between said fifth and sixth transistors, wherein said intermediate node of said blind detection circuit is coupled to a second column line.

According to another embodiment, a first main conducting node of said first transistor is coupled to a first of said differential output nodes of said antenna; and a first main conducting node of said second transistor is coupled to a second of said differential output nodes of said antenna, wherein second main conducting nodes of said first and second transistors are formed by a common semiconductor region.

According to another embodiment, the first and second transistors have channels formed in a common well.

According to another embodiment, the first and second transistors are each n-channel MOS transistors, and the channels are formed in a common p-type well, and the second main conducting nodes are source nodes formed by a common n-type region.

According to a further aspect, there is provided an image sensor comprising: an array of pixel circuits each comprising the above pixel circuit; and output circuitry adapted to perform analog to digital conversion of an output signal from each of said pixel circuits.

According to yet a further aspect, there is provided an electronic device comprising a processor; and an image sensor comprising an array of pixel circuits each comprising the above pixel circuit.

According to yet a further aspect, there is provided a method comprising: during a detection phase of a terahertz image sensor having a plurality of pixel circuits each including a detection circuit comprising first and second transistors coupled in series between differential output nodes of an antenna, applying a biasing voltage to control nodes of said first and second transistors; and during a reset phase of said terahertz image sensor, applying a reset voltage to the control nodes of said first and second transistors to reset the voltage stored by a capacitor coupled to an intermediate node between the first and second transistors.

According to an embodiment, applying the biasing voltage to the control nodes of said first and second transistors comprises activating a third transistor coupled between said gate biasing voltage and the control nodes of said first and second transistors; and applying said reset voltage to the control nodes of said first and second transistors comprises activating a second transistor coupled between said reset voltage and the control nodes of said first and second transistors.

According to another embodiment, the biasing voltage is in the range −0.4 V to 0.8 V, and the reset voltage is, for example, in the range 1 V to 2 V.

According to another embodiment, the method further comprises reading a voltage level stored by said capacitor of each pixel circuit, and reading a further voltage level stored by a further capacitor of each pixel circuit, said further capacitor being coupled an intermediate node between fifth and sixth transistors of a blind detection circuit of each pixel circuit.

BRIEF DESCRIPTION OF THE DRAWINGS

The foregoing and other purposes, features, aspects and advantages of the embodiments will become apparent from the following detailed description of embodiments, given by way of illustration and not limitation with reference to the accompanying drawings, in which.

DETAILED DESCRIPTION

Figure 1:
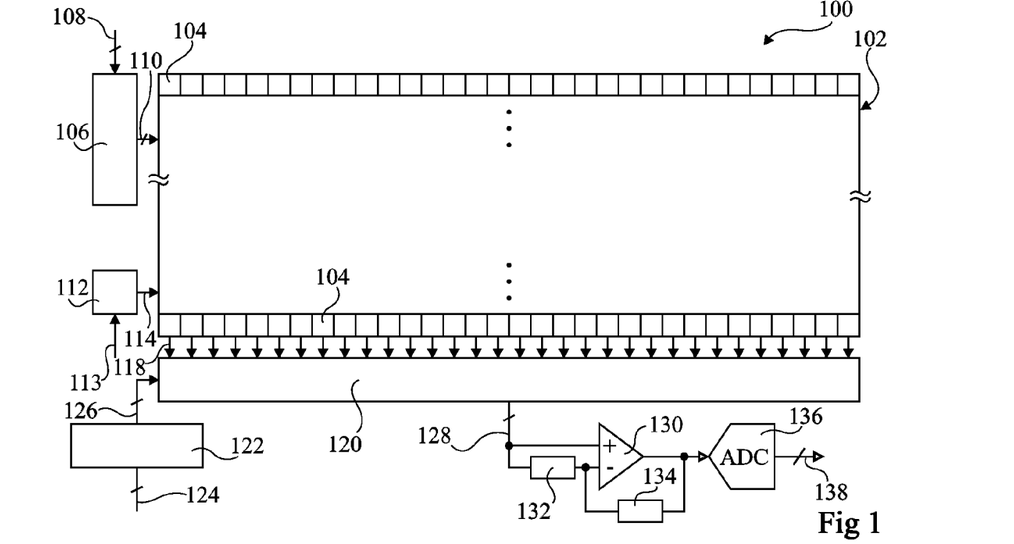
FIG. 1 illustrates a terahertz imager according to an example embodiment of the present disclosure.

FIG. 1 schematically illustrates a terahertz imager 100 according to an example embodiment.

The imager 100 comprises an image sensor formed of a 2-dimensional array 102 of pixel circuits 104. In the example of FIG. 1, the array 102 comprises 1024 pixel circuits arranged in 32 rows and 32 columns. Of course, it will be apparent to those skilled in the art that the pixel array 102 could be of a different size and/or aspect ratio. For example, the array 102 could comprise between 1 and several hundred rows and between 1 and several hundred columns of pixels.

The pixel array 102 is, for example, controlled in a similar fashion to the pixel array of a visible light image sensor. In particular, a row decoder 106 is, for example, provided, which receives a control signal on an input line 108 indicating a row to be read during a read phase of the pixel array 102. For example, in the case that there are 32 rows, the control signal on lines 108 is 5 bits wide. The row decoder 106 provides a corresponding row selection signal to a row line (not illustrated in FIG. 1) of each row of the pixel array 102.

A control block 112 is also, for example, provided, which receives a control signal on input line 113 for controlling the timing of a global or partial reset of the pixel array, as will be described in more detail below. The control block 112 provides a corresponding control signal on an output line 114 to each pixel circuit 104 of the pixel array 102.

The pixel array 102, for example, provides output signals on outputs 118, each comprising one or more column lines associated with each column of the pixel array 102. The outputs 118 are coupled to an output block 120 comprising active loads for driving each column line as well as switches for selecting columns, as will be described in more detail below.

In one embodiment, the columns are read in sequence, under control of a column decoder 122. The column decoder 122 receives a control signal on input lines 124 indicating a column to be read. Assuming that the pixel array 102 comprises 32 columns, the control signal on line 124 is, for example, 5 bits wide. The column decoder 122 provides a corresponding column selection signal on output lines 126 to control one or more switches of the output block 120 associated with each column of the pixel array 102.

The output block 120, for example, provides an output on output lines 128, of which there are one or more output lines associated with each column. The output block 120 provides an analog voltage level representing the values read from the pixel circuit of a selected row and column. The analog voltage values are, for example, provided to one or more output amplifier circuits. In the example of FIG. 1, an example of an amplifier circuit comprising an amplifier 130, for example an operational amplifier, is illustrated. A positive input of the amplifier 130 is coupled to the output lines 128, and the negative input of amplifier 130 is coupled to the output lines 128 via a resistor 132. The negative input is also coupled to the output of the amplifier 130 via a resistor 134. The output of the amplifier 130 is further coupled to an analog to digital converter (ADC) 136, which generates a digital value on output lines 138 based on the analog input voltage read from the pixel array 102. For example, the ADC is a ramp converter, which is well known in the art.

In alternative embodiments, the columns could be read in parallel, an amplifier and an ADC being provided for each column.

Of course, the amplifier circuit at the output of the pixel array could be implemented in many different ways as will be appreciated by those skilled in the art, the circuit illustrated in FIG. 1 being only one example.

Figure 2:
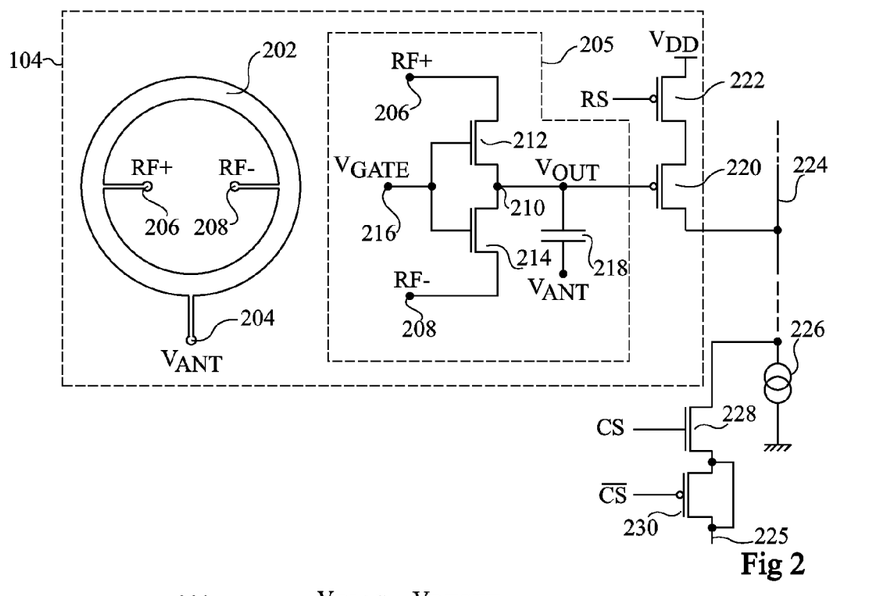
FIG. 2 illustrates a pixel circuit of the terahertz imager of FIG. 1 in more detail according to an example embodiment of the present disclosure.

FIG. 2 schematically illustrates a pixel circuit 104 of the pixel array 102 of FIG. 1 in more detail according to an example embodiment.

The pixel circuit 104 comprises an antenna 202, which in the example of FIG. 2 is a ring antenna. The antenna 202 comprises an input node 204 for receiving a biasing voltage VANT applied to the antenna via a supply rail (not illustrated in FIG. 2). Furthermore, the antenna 202 comprises differential output nodes 206 and 208, formed on opposite sides of the ring antenna, and, for example, formed at equal distances from the biasing input node 204. The output nodes 206 and 208 respectively provide positive and negative components RF+, RF− forming the differential output signal of the antenna 202.

In one embodiment, the ring antenna is formed of a conducting ring having an average diameter of between 50 and 200 μm, and the thickness of the ring between its inner and outer edges is, for example, between 5 and 25 μm.

The differential output nodes 206 and 208 of the antenna 202 are coupled to a differential detection circuit 205 of the pixel circuit 104. In particular, the node 206 is coupled to a node 210 of the detection circuit via the main current nodes of a transistor 212, and the node 208 is coupled to the node 210 via the main current nodes of a transistor 214. For example, transistors 212 and 214 are n-channel MOS (NMOS) transistors, and have their drains coupled to the differential output nodes 206 and 208 respectively, and their sources coupled together to the intermediate node 210. The control nodes of transistors 212 and 214 are coupled together to an input node 216 for receiving a gate control signal VGATE.

The intermediate node 210 is further coupled to a capacitor 218 of the detection circuit 205. The capacitor 218 is, for example, coupled between node 210 and the biasing voltage VANT, which is the same voltage level as applied to the input node 204 of antenna 202. The capacitor 218 stores an output voltage VOUT of the detection circuit 205. In one example, the capacitor 218 has a capacitance of between 1 pF and 100 pF.

The output voltage VOUT is, for example, read via read circuitry comprising a sense transistor 220, which is, for example, a p-channel MOS (PMOS) transistor, having its gate coupled to node 210. Transistor 220 has one of its main current nodes, for example its drain, coupled to a supply voltage VDD via a row selection transistor 222. Transistor 222 is controlled at its gate by a row selection signal RS, which, for example, corresponds to one of the signals provided on lines 110 of FIG. 1. The other main current node of transistor 220, for example its source, is coupled to a column line 224 associated with the pixel circuit 104 of FIG. 2.

The column line 224, for example, interconnects all the pixel circuits of the column. The column line 224 is, for example, coupled to a grounded current mirror 226. Furthermore, the column line 224 is, for example, coupled to an output line 225 of the circuit via a pair of transistors 228 and 230 coupled in series. Transistor 228 is, for example, an NMOS transistor controlled at its gate node by a column selection signal CS. Transistor 230 is, for example, a dummy PMOS transistor used for switching-noise reduction, shorted between its drain and source nodes, and coupled at its gate node to the inverse $\overline{CS}$ of the column selection signal CS. As an alternative, PMOS transistor 230 could be used without being shorted, and instead be coupled in parallel with transistor 228, such that together transistors 228 and 230 act as a transmission gate. The column selection signal CS provided to the output circuitry of each column correspond, for example, to the signals provided on lines 126 of FIG. 1 to the output block 120, and the output lines 225 of each column, for example, correspond to the lines 128 of the output block 120 of FIG. 1.

In operation, the gate voltage VGATE applied via node 216 to the gates of transistors 212 and 214 of the detection circuit is at either a biasing level used to activate the transistors 212 and 214 during a detection mode of the image sensor, or a reset level, for example higher than the biasing level in the case that transistors 212 and 214 are NMOS transistors. The reset voltage is used to reset the voltage on the capacitor 218, as will now be described with reference to FIG. 3.

Figure 3:
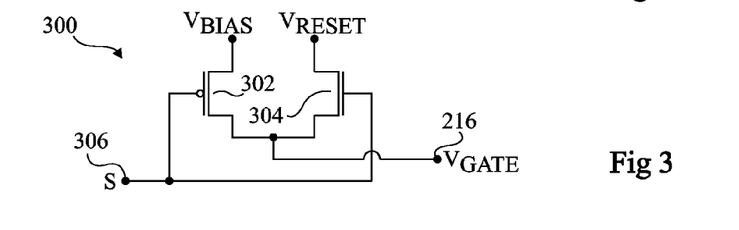
FIG. 3 illustrates circuitry for generating a gate voltage of the circuitry of FIG. 2 according to an example embodiment of the present disclosure.

FIG. 3 illustrates an example circuit 300 for generating the gate biasing voltage VGATE applied to the node 216 coupled to the control nodes of transistors 212 and 214 of the detection circuit 205 of FIG. 2.

Node 216 is coupled to a biasing voltage VBIAS via the main current nodes of a transistor 302, which in this example is a PMOS transistor, and to a reset voltage VRESET via the main current nodes of a transistor 304, which in this example is an NMOS transistor.

The gates of transistors 302, 304 are both coupled to an input line 306 receiving a control signal S. The control signal S is, for example, provided on line 114 of FIG. 1 and generated by the control block 112. When the control signal S is low, the node 216 is coupled to the biasing voltage VBIAS, whereas when the signal S is high, the node 216 is coupled to the reset voltage VRESET. Thus the control signal S is, for example, a shutter signal controlling when a global or partial reset of the pixel array is to be performed.

In alternative embodiments, the transistors 302, 304 could both be NMOS or PMOS transistors respectively receiving at their gates the control signal S and its inverse $\overline{S}$.

In some embodiments, each pixel circuit 104 of the pixel array 102 receives the gate voltage signal VGATE from a corresponding circuit 300. Alternatively, one or more circuits 300 could each provide the gate voltage signal VGATE to a plurality of pixel circuits, for example to all of the pixel circuits of a row of the pixel array 102.

In operation, during a detection phase of the pixel array 102, the selection signal S, for example, selects the biasing voltage VBIAS to be applied as the voltage signal VGATE to all of the pixel circuits of the array 102. The biasing voltage VBIAS is, for example, in the range −0.4 V to 0.8 V. This biasing voltage, for example, places the transistors 212 and 214 of each detection circuit 205 in the triode or linear region of operation, such that the transistors operate in a similar fashion to resistors, and the current conducted by the transistors is proportional to the gate drain voltage. Transistors 212 and 214 could also operate in the sub-threshold region, for example corresponding to a gate voltage of between 0 V and the threshold voltage VTH, where the transistors are for example highly nonlinear. It will be apparent to those skilled in the art that the level of the biasing voltage VBIAS will depend on the threshold voltages VTH of the transistors 212 and 214, and also on the amplitude of the signals present on the antenna, and on the desired noise performance and impedance matching preferences. During the detection phase, the capacitor 218 of each detection circuit 205 is charged based on the level of the detected terahertz radiation falling on the antenna 202.

During a reset phase, for example at the end of the detection phase, a global or partial reset of the pixel array 102 is performed. In some embodiments, a global reset is performed to reset all of the pixel circuits of the pixel array. In alternative embodiments, a rolling shutter operation could be applied, according to which the pixel circuits are reset row by row. Advantageously, the global or partial reset is performed by selecting by the selection signal S to apply the reset voltage VRESET as the gate voltage VGATE to all of the pixel circuits to be reset. The reset voltage VRESET is, for example, in the range 1 V to 2 V. Such a voltage level is chosen to fully activate the transistors 212 and 214 as open switches rather than detectors, such that the voltage stored by the capacitor 218 is discharged to the antenna 202. It will be apparent to those skilled in the art that the reset voltage will be chosen based, for example, on the threshold voltages VTH of the transistors 212 and 214.

Figure 4:
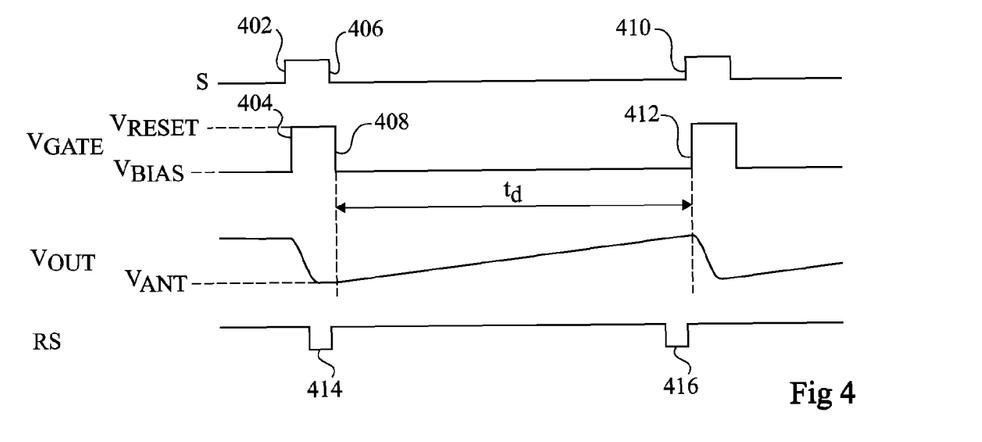
FIG. 4 is a timing diagram illustrating signals in the circuitry of FIGS. 2 and 3 according to an example embodiment of the present disclosure.

FIG. 4 is a timing diagram showing examples of signals present in the circuits of FIGS. 2 and 3. In particular, FIG. 4 shows examples of the selection signal S, the gate voltage signal VGATE, the output voltage VOUT and the row selection signal RS.

As illustrated, the control signal S is initially low, and goes high at a rising edge 402. This triggers, shortly afterwards, a rising edge 404 of the gate voltage signal VGATE, which transitions from the bias level VBIAS to the reset level VRESET. In one example, the bias voltage is at 0.5 V, and the reset voltage is at the supply voltage VDD of the pixel array, which is, for example, at 1.1 volts. As illustrated, in response to the rising edge 404 of the gate voltage signal VGATE, the output voltage VOUT drops progressively to the level VANT, its voltage being discharged via the antenna 202 and its input node 204.

A falling edge 406 of the control signal S then triggers, shortly afterwards, a transition 408 of the gate voltage signal VGATE from the reset level VRESET back to the bias level VBIAS. This transition 408 initiates a detection phase td of the pixel circuit, during which the output voltage VOUT rises progressively from the level of voltage VANT until an end of the detection phase td. At the end of the detection phase td, a rising edge 410 of the control signal S causes, shortly thereafter, a transition 412 of the gate voltage signal VGATE to the reset voltage VRESET. This causes a further reset of the output voltage, which falls back to the level of voltage VANT, for example before the start of a new detection phase.

The row selection signal RS controls when the voltage VOUT stored by the capacitor 218 is read via the column line 224. When the row of the pixel circuit is not being read, the row selection signal RS is, for example, at a logic high, such that the PMOS transistor 222 is non-conducting. In one example, the row selection signal RS has a low pulse 414 just before the start of the detection phase td in order to read a reference value from the capacitor 218, and a further low pulse 416 at the end of the detection phase td just before the reset voltage is asserted in order to read the final output voltage stored by the capacitor 218.

Figure 5:
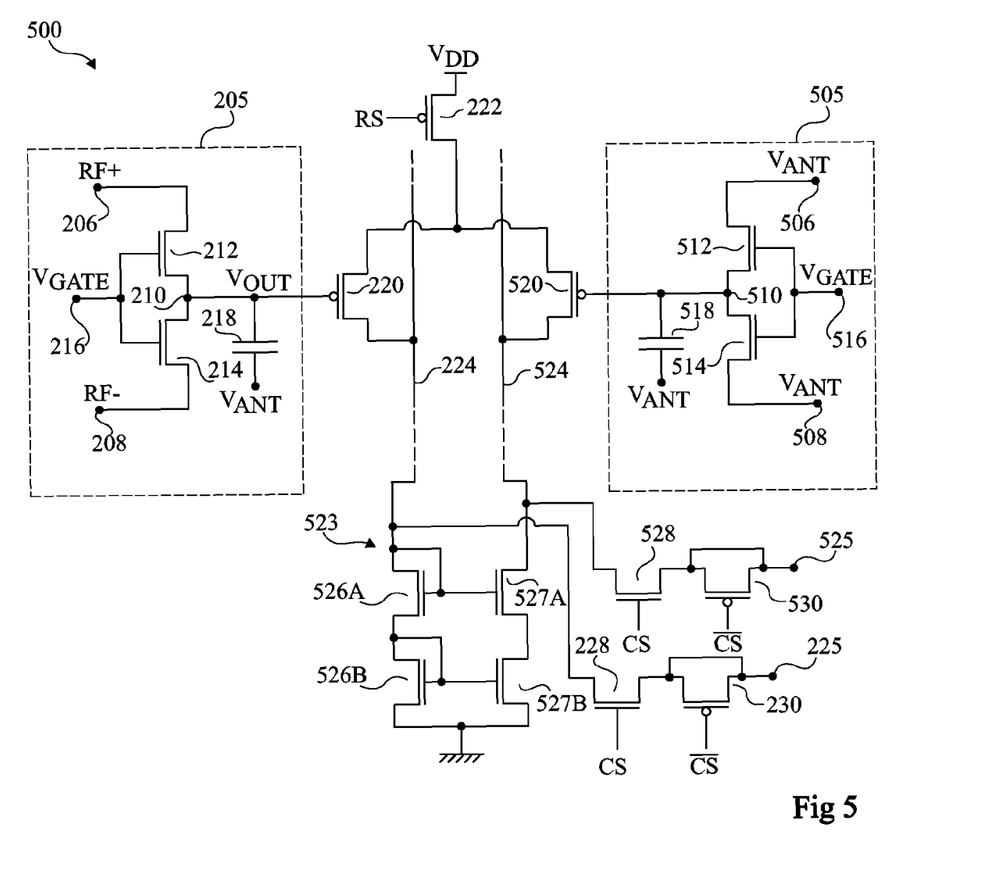
FIG. 5 illustrates a pixel circuit of the terahertz imager of FIG. 1 in more detail according to a further example embodiment of the present disclosure.

FIG. 5 illustrates a pixel circuit 500 according to a further embodiment.

The pixel circuit 500 comprises the same differential detection circuit 205 as that of FIG. 2, which is also coupled to the antenna 202 (not illustrated in FIG. 5), and this detection circuit will not be described again in detail. The pixel circuit 500 further comprises a blind differential detection circuit 505. The blind detection circuit 505 is very similar to the detection circuit 205. In particular, it comprises differential nodes 506 and 508, of which node 506 is coupled to a node 510 via the main current nodes of a transistor 512, and node 508 is coupled to the node 510 via the main current nodes of a transistor 514. For example, transistors 512 and 514 are n-channel MOS (NMOS) transistors, and have their drains coupled to the differential nodes 506 and 508 respectively, and their sources coupled together to the intermediate node 510. Furthermore, the control nodes of transistors 512 and 514 are coupled together to an input node 516, and both transistors receive the gate voltage signal VGATE via the input node 516, in a similar fashion to transistors 212 and 214. However, rather than being coupled to differential output nodes of an antenna, the nodes 506 and 508 of the blind detection circuit 505 are, for example, coupled to the antenna biasing voltage VANT.

The blind detection circuitry 505 thus provides a reference value, generated in exactly the same way as the signal generated by transistors 212 and 214 of the detector, except that there is no antenna, and therefore no terahertz signal present.

Read circuitry for reading the voltages stored by capacitors 218 and 518 of the detection circuit 205 and the blind detection circuit 505, for example, comprises the sense transistor 220 having its gate coupled to the node 210, and a further sense transistor 520 having its gate coupled to the node 510. Both of the transistors 220 and 520 are, for example, PMOS transistors. The drains of transistors 220 and 520 are each, for example, coupled to the supply voltage VDD via the main current nodes of a single row selection transistor 222. The sources of transistors 220 and 520 are, for example, coupled to column lines 224 and 524 respectively.

The column lines 224 and 524 are, for example, coupled to all of the pixel circuits of the column. Furthermore, the column lines 225 and 524 are coupled to a current mirror 523. The current mirror 523, for example, comprises a first branch comprising transistors 526A, 526B coupled in series by their main current nodes between column line 224 and ground, and a second branch comprising transistors 527A and 527B coupled in series by their main current nodes between column line 524 and ground. The transistors 526A, 526B, 527A, 527B are all, for example, NMOS transistors. The gates of transistors 526A and 527A are, for example, coupled together and to the column line 224. The gates of transistors 526B and 527B are, for example, coupled together and to the intermediate node between the transistors 526A and 526B.

As with the embodiment of FIG. 2, the column line 224 is further coupled to the output line 225 via the transistors 228 and 230 coupled in series. Similarly, the column line 524 is coupled to an output line 525 via transistors 528 and 530 coupled in series. As with transistors 228 and 230, transistor 528 is, for example, an NMOS transistor receiving at its gate a column selection signal CS, and transistor 530 is a drain-source shorted PMOS transistor receiving at its gate the column selection signal $\overline{CS}$. As with transistor 230, in alternative embodiments, the PMOS transistor 530 could be used without being shorted, and instead be coupled in parallel with transistor 528, such that together transistors 528 and 530 act as a transmission gate.

In operation, when the column selection signal CS and row selection signal RS of the pixel circuit 500 are asserted at the end of a detection phase, the voltage stored on capacitor 218 is transferred to the output line 225, while the voltage stored on capacitor 518 is transferred to the output line 525. The signal from the blind detection circuit 505 will substantially represent noise, which can be subtracted from the signal from the detection circuit 205 in order to improve the signal to noise ratio of this signal.

Figure 6:
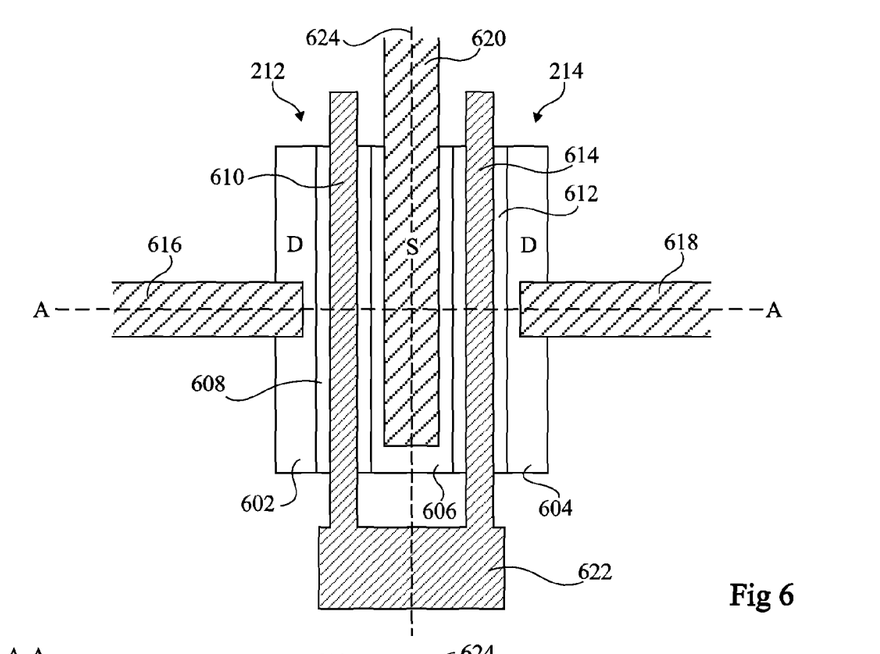
FIG. 6 illustrates, in plan view, the layout of transistors of a differential detection circuit of the pixel circuit of FIGS. 2 and 5 according to an example embodiment of the present disclosure.

FIG. 6 is a plan view representing the layout of the transistors 212 and 214 of FIGS. 2 and 5 according to an example embodiment. The transistors 512 and 514 of FIG. 5 are, for example, formed having the same layout.

As illustrated, the transistors 212 and 214 are, for example, formed as a single device having separate drain regions 602 and 604 and a common source region 606. The drain 602 is formed on one side of a gate 608 of transistor 212 having a gate contact 610. The source region 606 is formed on the opposite side of the gate 608 from the drain 602. Transistor 214 has a gate 612 having a gate contact 614. The drain region 604 is formed on the opposite side of the gate 612 from the source region 606.

A drain connection 616 makes contact with the drain region 602, and similarly, a drain connection 618 makes contact with the drain region 604. A source connection 620 makes contact with the central source region 606.

The gate contacts 610 and 614 of transistors 212 and 214 respectively form fingers in parallel with each other, and connected at one end to a connection zone 622.

A line of symmetry passes through the device, represented by the dashed line 624 in FIG. 6, which runs through the center of the source region 606 and the source connection 620 between the transistors, and through the center of the gate connection zone 622. This line represents a virtual AC (alternating current) ground of the device.

Figure 7:
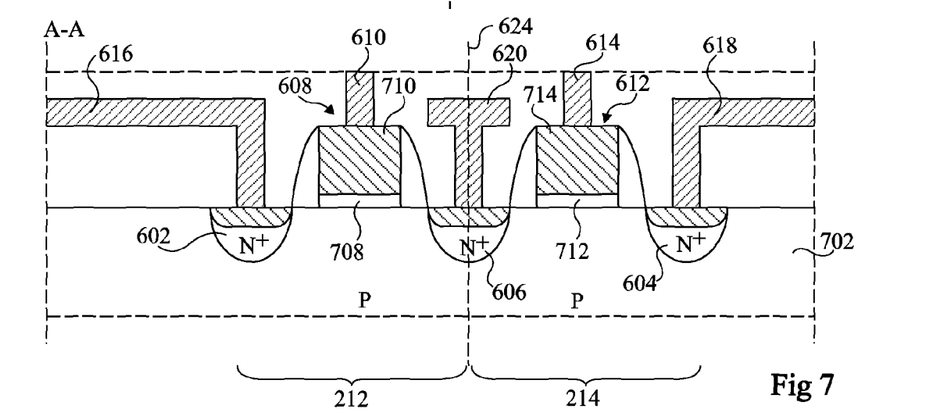
FIG. 7 is a cross-section view of the transistors of FIG. 6 according to an example embodiment of the present disclosure.

FIG. 7 is a cross-section view corresponding to a cross-section of the device of FIG. 6 taken along a line A-A shown by a dashed line in FIG. 6, passing perpendicular to the drain and source regions 602, 604 and to the gate contacts 610, 614.

As illustrated in FIG. 7, the structure, for example, comprises a p-type well 702, for example surrounded by isolation trenches (not illustrated in FIG. 7) having formed at its upper surface a heavily doped n-type region 602 forming the drain of transistor 212, a heavily doped n-type region 604 forming the drain of transistor 214, and a heavily doped n-type region 606 positioned between the n-type regions 602, 604 and forming the common source of the device. A top portion of each of the n-type regions 602, 604 and 606 is, for example, silicided, allowing contact with corresponding metal contacts.

The gate 608 of transistor 212 comprises a gate stack positioned between the n-type regions 602 and 606. The gate 612 of transistor 214 comprises a gate stack positioned between the n-type regions 606 and 604. The gate stack of gate 608 comprises an insulating layer 708 formed over the p-type well 702, and a gate electrode 710 formed over the insulating layer 708. The gate electrode 710 is, for example, formed of a metal silicide. The gate contact 610 makes contact with the gate electrode 710. Similarly, the gate stack of gate 612, for example, comprises an insulating layer 712 formed over the p-type well 702, and a gate electrode 714 formed over the insulating layer 712. The gate electrode 714 is, for example, formed of a metal silicide. The gate contact 614 makes contact with the gate electrode 710. Spacers are represented on the each side of the gate stacks of each of the gates 608 and 612.

Thus the two-transistor structure has a symmetry on each side of the dashed line 624 shown in the center of the device in FIG. 7, which passes through the common source contact 612 and the common source region 606 of the transistors and the intersection of the contacts of the two gate-fingers. An advantage of such a structure is that this symmetry automatically leads to a virtual AC ground being present in the source region 606 and source contact 612 with respect to the differential signals present on the drain contacts 616 and 618. This level is referred to herein as a "virtual AC ground" because it is a common-mode AC ground level due to the differential topology, which may or may not be at 0 V DC (direct current). This virtual AC ground is also present at the line of intersection of the contacts of the gate-fingers, meaning that the terahertz radiation is presented across the gate-source and drain-source regions simultaneously, due to the common virtual AC ground. This results in an inherent self-mixing of the terahertz signal resulting from the device geometry, and across both of the differential inputs of the detector.

Figure 8:
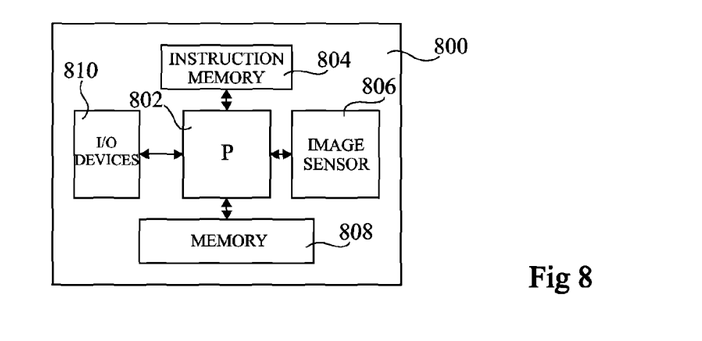
FIG. 8 illustrates an electronics device according to an example embodiment of the present disclosure.

FIG. 8 schematically illustrates a terahertz device 800 according to an example embodiment.

The device 800 comprises a processor 802 coupled to an instruction memory 804. In particular, the processor 802 is, for example, under control of the instructions stored in the instruction memory. An image sensor 806 is coupled to the processor, and, for example, comprises the terahertz image sensor 100 of FIG. 1, comprising pixel circuits according to the embodiment of FIG. 2 or 5. Furthermore, a memory 808, which is, for example, a non-volatile memory, provides storage space for storing captured images transferred from the image sensor. One or more input/output devices 810, such as touch screens or keyboards, may also be in communication with the processor 802.

An advantage of the embodiments of the pixel circuit of FIGS. 2 and 5 comprising the control circuitry such as that of FIG. 3 for applying a reset function is that the pixel circuits can be reset in a simple fashion with little added noise. Furthermore, by allowing the pixel circuits to be reset periodically, the signal to noise ratio of the output signal of each pixel circuit can be improved. In particular, for pixel circuits of the terahertz type, the noise at the output tends to reduce as the capacitance of the capacitor of the detection circuit is increased. However, the size of the capacitor present in each pixel is limited by the overall size of the image sensor. Periodically resetting the voltage stored by the capacitor leads to a noise-reducing effect similar to that of increasing the capacitor size, and permits a relatively small capacitance to be used.

An advantage of using a blinded detection circuit as described with relation to FIG. 5 is that further noise can be extracted from the output signal of the pixel circuit. Advantageously, the blinded pixel circuit has its antenna inputs coupled to an antenna biasing voltage rather than to an antenna, and thus it is not necessary to shield an antenna from radiation, which would be particularly problematic for an antenna receiving a terahertz signal.

An advantage of the embodiment of FIGS. 6 and 7, according to which transistors of the detection circuit of each pixel circuit are formed of a device having a common source, is that this leads to a particularly well-adjusted virtual AC ground level with respect to the differential signals from the antenna, leading to mixing of the terahertz radiation with high efficiency.

Having thus described at least one illustrative embodiment, various alterations, modifications and improvements will readily occur to those skilled in the art.

For example, while in the embodiment of FIG. 2 an example of the shape of an antenna has been represented, it will be apparent to those skilled in the art that various different shapes and layouts could be used.

Furthermore, while FIG. 3 illustrates an example of control circuitry for selectively applying the biasing voltage or reset voltage to the gate node 216, it will be apparent to those skilled in the art that various other implementations of this circuitry would be possible. For example, the transistor 302 could be replaced by an NMOS transistor and the transistor 304 by a PMOS transistor. Furthermore, the switch formed by transistors 302 and 304 could be further implemented by additional transistors coupled in parallel with transistors 302 and 304.

Furthermore, it will be apparent to those skilled in the art that, which the embodiments of the present disclosure have been described with reference to MOS transistor technology, the principles could be applied to other transistor technologies, such as bipolar technology.

Furthermore, it will be apparent to those skilled in the art that the levels referred to as a ground or virtual AC ground voltages could be at 0 V DC or at another voltage level.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. A pixel circuit comprising:
    a detection circuit having first and second transistors coupled in series between differential output nodes of an antenna, wherein said antenna is configured to be sensitive to terahertz radiation;
    a capacitor coupled to an intermediate node between said first and second transistors; and
    control circuitry coupled to control nodes of said first and second transistors, the control circuitry being configured for selectively applying to said control nodes one of:
        a gate biasing voltage for biasing the control nodes of the first and second transistors during a detection phase of the pixel circuit; and
        a reset voltage for resetting a voltage stored by said capacitor.

2. The pixel circuit of claim 1, wherein said control circuitry comprises:
    a third transistor coupled between said gate biasing voltage and the control nodes of said first and second transistors and having a control node coupled to a selection signal; and
    a fourth transistor coupled between said reset voltage and the control nodes of said first and second transistors and having a control node coupled to said selection signal.

3. The pixel circuit of claim 2, wherein one of the third and fourth transistors is a p-channel MOS transistor and the other of the first and second transistors is an n-channel MOS transistor.

4. The pixel circuit of claim 1, wherein said biasing voltage is in the range −0.4 V to 0.8 V and said reset voltage is in the range 1 V to 2 V.

5. The pixel circuit of claim 1, wherein said intermediate node is coupled to a first column line.

6. The pixel circuit of claim 5, further comprising:
a blind detection circuit having fifth and sixth transistors coupled in series between first and second nodes, said first and second nodes each being coupled to a biasing voltage of said antenna; and
a capacitor coupled to an intermediate node between said fifth and sixth transistors, wherein said intermediate node of said blind detection circuit is coupled to a second column line.

7. The pixel circuit of claim 1, wherein:
a first conducting node of said first transistor is coupled to a first of said differential output nodes of said antenna; and
a first conducting node of said second transistor is coupled to a second of said differential output nodes of said antenna, wherein second main conducting nodes of said first and second transistors are formed by a common semiconductor region.

8. The pixel circuit of claim 7, wherein said first and second transistors have channels formed in a common well.

9. The pixel circuit of claim 8, wherein said first and second transistors are each n-channel MOS transistors, and wherein said channels are formed in a common p-type well, and wherein said second main conducting nodes are source nodes formed by a common n-type region.

10. An image sensor comprising:
an array of pixel circuits each comprising the pixel circuit of claim 1; and
output circuitry adapted to perform analog to digital conversion of an output signal from each of said pixel circuits.

11. An electronic device comprising:
a processor; and
an image sensor coupled to said processor and comprising an array of pixel circuits each comprising the pixel circuit of claim 1.

12. A method comprising:
during a detection phase of a terahertz image sensor having a plurality of pixel circuits each including a detection circuit comprising first and second transistors coupled in series between differential output nodes of an antenna, applying a biasing voltage to control nodes of said first and second transistors; and
during a reset phase of said terahertz image sensor, applying a reset voltage to the control nodes of said first and second transistors to reset the voltage stored by a capacitor coupled to an intermediate node between the first and second transistors.

13. The method of claim 12, wherein:
applying said biasing voltage to the control nodes of said first and second transistors comprises activating a third transistor coupled between said gate biasing voltage and the control nodes of said first and second transistors; and
applying said reset voltage to the control nodes of said first and second transistors comprises activating as fourth transistor coupled between said reset voltage and the control nodes of said first and second transistors.

14. The method of claim 12, wherein said biasing voltage is in the range −0.4 V to 0.8 V and said reset voltage is in the range 1 V to 2 V.

15. The method of claim 12, further comprising reading a voltage level stored by said capacitor of each pixel circuit, and reading a further voltage level stored by a further capacitor of each pixel circuit, said further capacitor being coupled to an intermediate node between fifth and sixth transistors of a blind detection circuit of each pixel circuit.

* * * * *

UNITED STATES PATENT AND TRADEMARK OFFICE
CERTIFICATE OF CORRECTION

| | | |
|---|---|---|
| PATENT NO. | : 8,907,284 B2 | Page 1 of 1 |
| APPLICATION NO. | : 13/692691 | |
| DATED | : December 9, 2014 | |
| INVENTOR(S) | : Sherry et al. | |

It is certified that error appears in the above-identified patent and that said Letters Patent is hereby corrected as shown below:

In the claims,

Column 12, Line 23    Delete: "as fourth"
                      Insert: --a fourth--

Signed and Sealed this
Fifth Day of April, 2016

Michelle K. Lee
*Director of the United States Patent and Trademark Office*